US012746322B2

(12) United States Patent
Jain et al.

(10) Patent No.: US 12,746,322 B2
(45) Date of Patent: Sep. 29, 2026

(54) MEDICAL DEVICES AND RELATED SYSTEMS AND METHODS

(71) Applicants: BOSTON SCIENTIFIC SCIMED, INC., Maple Grove, MN (US); BOSTON SCIENTIFIC MEDICAL DEVICE LIMITED, Galway (IE)

(72) Inventors: Samriddhi Jain, New Delhi (IN); Shrikant Vasant Raut, Pune (IN); Arun Adhikarath Balan, Aluva (IN); Richard C. Tah, Milford, MA (US); Subodh Ramesh Morey, Ponda (IN); Rajivkumar Singh, Pune (IN); Niraj Prasad Rauniyar, Plymouth, MN (US)

(73) Assignees: BOSTON SCIENTIFIC SCIMED, INC., Maple Grove, MN (US); BOSTON SCIENTIFIC MEDICAL DEVICE LIMITED, Galway (IE)

(*) Notice: Subject to any disclaimer, the term of this patent is extended or adjusted under 35 U.S.C. 154(b) by 0 days.

(21) Appl. No.: 19/292,361

(22) Filed: Aug. 6, 2025

(65) Prior Publication Data

US 2026/0041835 A1 Feb. 12, 2026

Related U.S. Application Data

(60) Provisional application No. 63/680,851, filed on Aug. 8, 2024.

(51) Int. Cl.
*A61M 1/00* (2006.01)

(52) U.S. Cl.
CPC ............ *A61M 1/743* (2021.05); *A61M 1/774* (2021.05)

(58) Field of Classification Search
CPC .. A61B 1/00068; A61B 1/015; A61M 39/223; A61M 2039/224; A61M 1/77; A61M 1/772; A61M 1/774; A61M 1/741; A61M 1/75; A61M 2005/16863; A61M 2005/16868; A61M 2005/16872;
(Continued)

(56) References Cited

U.S. PATENT DOCUMENTS 2,991,804 A * 7/1961 Merkle ................ B60G 17/033 267/64.11
4,653,537 A * 3/1987 Voith .................. F16K 11/0836 137/625.43
(Continued)

*Primary Examiner* — William H Rodriguez
(74) *Attorney, Agent, or Firm* — Bookoff McAndrews, PLLC

(57) ABSTRACT

Medical devices and systems are described, including a medical device including a handle with a first conduit and a second conduit each coupled to a valve assembly. The valve assembly includes an inner body movable within an outer body between a first configuration and a second configuration. The outer body includes a first fluidics channel adjacent to a third fluidics channel on a first side, and a second fluidics channel adjacent to a fourth fluidics channel on a second side, opposite the first side. In the first configuration, the first and second fluidics channels and the first conduit are in communication, and the third and fourth fluidics channels and the second conduit are in communication. In the second configuration, the first and third fluidics channels and the first conduit are in communication, and the second and fourth fluidics channels and the second conduit are in communication.

20 Claims, 9 Drawing Sheets

(58) Field of Classification Search
CPC .... A61M 2005/3337; Y10T 137/86839; F16K 11/0716; F16K 11/07; F16K 11/065; F16K 11/06
See application file for complete search history.

(56) References Cited

U.S. PATENT DOCUMENTS

| | | | | | |
|---|---|---|---|---|---|
| 5,027,791 | A | 7/1991 | Takahashi | | |
| 5,354,291 | A * | 10/1994 | Bales | A61M 1/7415 | 604/35 |
| 5,687,764 | A * | 11/1997 | Tanaka | F16K 11/0525 | 137/625.43 |
| 5,795,403 | A | 8/1998 | Biermaier | | |
| 6,289,931 | B1 * | 9/2001 | Sisk | F25B 41/26 | 137/625.43 |
| 6,295,828 | B1 * | 10/2001 | Koo | F16K 11/0525 | 137/625.29 |
| 11,655,905 | B2 * | 5/2023 | Ledvora | F16K 11/0853 | 137/625.46 |
| 2003/0018290 | A1 * | 1/2003 | Brugger | A61M 39/223 | 604/6.1 |
| 2006/0037654 | A1 * | 2/2006 | Moreno | F16K 11/074 | 137/625.43 |
| 2012/0085956 | A1 * | 4/2012 | Morimoto | A61B 8/445 | 251/324 |
| 2014/0090414 | A1 * | 4/2014 | McLane | F16K 5/0471 | 62/115 |
| 2015/0144215 | A1 * | 5/2015 | Bellofatto | F16K 11/0712 | 137/625.69 |
| 2019/0350441 | A1 | 11/2019 | Saiga | | |
| 2020/0187756 | A1 | 6/2020 | Maurice | | |
| 2020/0200440 | A1 * | 6/2020 | Bates | F16K 31/50 | |
| 2020/0355281 | A1 * | 11/2020 | Harris | A61B 90/70 | |
| 2021/0298567 | A1 * | 9/2021 | Comee | A61B 1/015 | |
| 2021/0298572 | A1 * | 9/2021 | Comee | A61B 1/015 | |
| 2022/0133131 | A1 * | 5/2022 | Busch | A61B 1/05 | 600/159 |
| 2022/0240943 | A1 * | 8/2022 | Levy | A61B 17/12186 | |
| 2023/0172430 | A1 * | 6/2023 | Wales | A61B 1/015 | 600/159 |
| 2024/0032774 | A1 * | 2/2024 | Comee | A61B 1/00068 | |
| 2024/0049945 | A1 * | 2/2024 | Harris | A61B 1/015 | |
| 2024/0358227 | A1 * | 10/2024 | Lammers | A61B 1/126 | |
| 2025/0064300 | A1 * | 2/2025 | Ramos Espinoza | A61B 1/00068 | |
| 2025/0082177 | A1 * | 3/2025 | Ramos Espinoza | A61B 1/0011 | |
| 2025/0113992 | A1 * | 4/2025 | Noyes | A61B 1/00094 | |
| 2025/0134350 | A1 * | 5/2025 | Cummings | A61B 1/12 | |
| 2025/0255463 | A1 * | 8/2025 | Scutti | A61B 1/00068 | |
| 2025/0344944 | A1 * | 11/2025 | Noyes | A61B 1/018 | |

* cited by examiner

MEDICAL DEVICES AND RELATED SYSTEMS AND METHODS

CROSS-REFERENCE TO RELATED APPLICATION(S)

This application claims the benefit of priority to U.S. Provisional Application No. 63/680,851, filed on Aug. 8, 2024, which is incorporated by reference herein in its entirety.

TECHNICAL FIELD

Aspects of the present disclosure generally relate to medical devices and medical systems. In particular, some aspects relate to medical devices and systems having a handle with a valve assembly to control fluid delivery and aspiration.

BACKGROUND

Medical devices such as scopes and sheaths are often inserted into the body of a patient to perform a therapeutic and/or diagnostic procedure inside the body. Various features of the scope and/or sheath may assist in performing a therapeutic and/or diagnostic procedure inside the subject's body, e.g., including supply of irrigation or suction. When applying suction to a target site, materials may become lodged within a suction channel. Lodged materials may form a blockage within the suction channel, which may reduce a magnitude of negative pressure applied at the target site. Blockages within the suction channel may require the medical device to be removed from the patient's body in order for an operator to clear the blockages. Removing the medical device to clear blockages may increase a duration of a procedure and may increase risk for the patient.

SUMMARY

Each of the aspects disclosed herein may include one or more features described in connection with any of the other disclosed aspects.

The present disclosure includes medical devices and methods of use thereof, including a medical device comprising a handle and a valve assembly. The handle may comprise a first conduit and a second conduit each coupled to the valve assembly within a housing of the handle. The valve assembly may comprise an outer body and an inner body movable within the outer body. The outer body may include a first fluidics channel adjacent to a third fluidics channel on a first side of the outer body, and a second fluidics channel adjacent to a fourth fluidics channel on a second side of the outer body opposite to the first side. The valve assembly may include a first configuration wherein the first fluidics channel and the second fluidics channel are in fluid communication with each other and the first conduit, and the third fluidics channel and the fourth fluidics channel are in fluid communication with each other and with the second conduit. In a second configuration of the valve assembly, the first fluidics channel and the third fluidics channel may be in fluid communication with each other and the first conduit, and the second fluidics channel and the fourth fluidics channel may be in fluid communication with each other and the second conduit. Moving the inner body relative to the outer body may transition the valve assembly between the first configuration and the second configuration.

According to some aspects of the present disclosure, the inner body may be slidable or rotatable within an opening of the outer body. An end of the inner body may define an actuator of the handle, e.g., the end of the inner body coupled to the housing of the handle and configured to receive user input to transition the valve assembly between the first configuration and the second configuration. One of the first conduit or the second conduit may include a port configured to be coupled to a source of fluid, and the other of the first conduit or second conduit may include a port configured to be coupled to a vacuum source. According to some aspects, the inner body may define two first lumens extending along an outer surface of the inner body. Additionally or alternatively, in the first configuration, one of the first lumens may be in fluid communication with the first conduit and the other of the first lumens may be in fluid communication with the second conduit. Optionally, the valve assembly may include a biasing element that biases the inner body to the first configuration.

In some examples, the housing may include a fluid inlet and an aspiration outlet. According to some aspects, the fluid inlet may be connected to the first fluidics channel and the aspiration outlet may be connected to the fourth fluidics channel in both the first configuration and the second configuration of the valve assembly. The medical device may further comprise a shaft coupled to the handle, e.g., the shaft defining a fluid channel and a suction channel each coupled to the valve assembly.

In some examples, the inner body may define two first lumens with portions parallel to each other. In the first configuration, one of the first lumens may be in fluid communication with the first conduit and the other of the first lumens may be in fluid communication with the second conduit. Additionally or alternatively, the inner body may define two second lumens with portions parallel to each other. In the second configuration, one of the second lumens may be in fluid communication with the first conduit and the other of the second lumens may be in fluid communication with the second conduit. According to some aspects, the two first lumens may be perpendicular to portions of the two second lumens. In some aspects, the two first lumens may be staggered with the two second lumens.

The present disclosure also includes a medical device comprising a handle and a valve assembly with at least some of the features discussed above and elsewhere herein. For example, the handle may comprise a first conduit and a second conduit each coupled to the valve assembly within a housing of the handle, wherein the valve assembly comprises an outer body and an inner body slidable or rotatable within the outer body. An end of the inner body may be coupled to the housing and may be configured to receive user input, e.g., to control the valve assembly. The outer body may include a first fluidics channel adjacent to a third fluidics channel on a first side of the outer body, and a second fluidics channel adjacent to a fourth fluidics channel on a second side of the outer body opposite to the first side. The valve assembly may include a first configuration and a second configuration. In the first configuration, the first fluidics channel and the second fluidics channel may be in fluid communication with each other and with the first conduit, and the third fluidics channel and the fourth fluidics channel may be in fluid communication with each other and with the second conduit. In the second configuration, the first fluidics channel and the third fluidics channel may be in fluid communication with each other and with the first conduit, and the second fluidics channel and the fourth fluidics channel may be in fluidic communication with each other and with the second conduit. Moving the inner body relative to the outer body by user input may transition the valve assembly between the first configuration and the second configuration. The housing may include a fluid inlet and an aspiration outlet. For example, the fluid inlet may be connected to the first fluidics channel and the aspiration outlet may be connected to the fourth fluidics channel in both the first configuration and the second configuration of the valve assembly.

BRIEF DESCRIPTION OF THE FIGURES

The accompanying drawings, which are incorporated in and constitute a part of this application, illustrate exemplary aspects that, together with the written descriptions, serve to explain the principles of this disclosure. Each figure depicts one or more exemplary aspects according to this disclosure, as follows.

DETAILED DESCRIPTION

Figure 1:
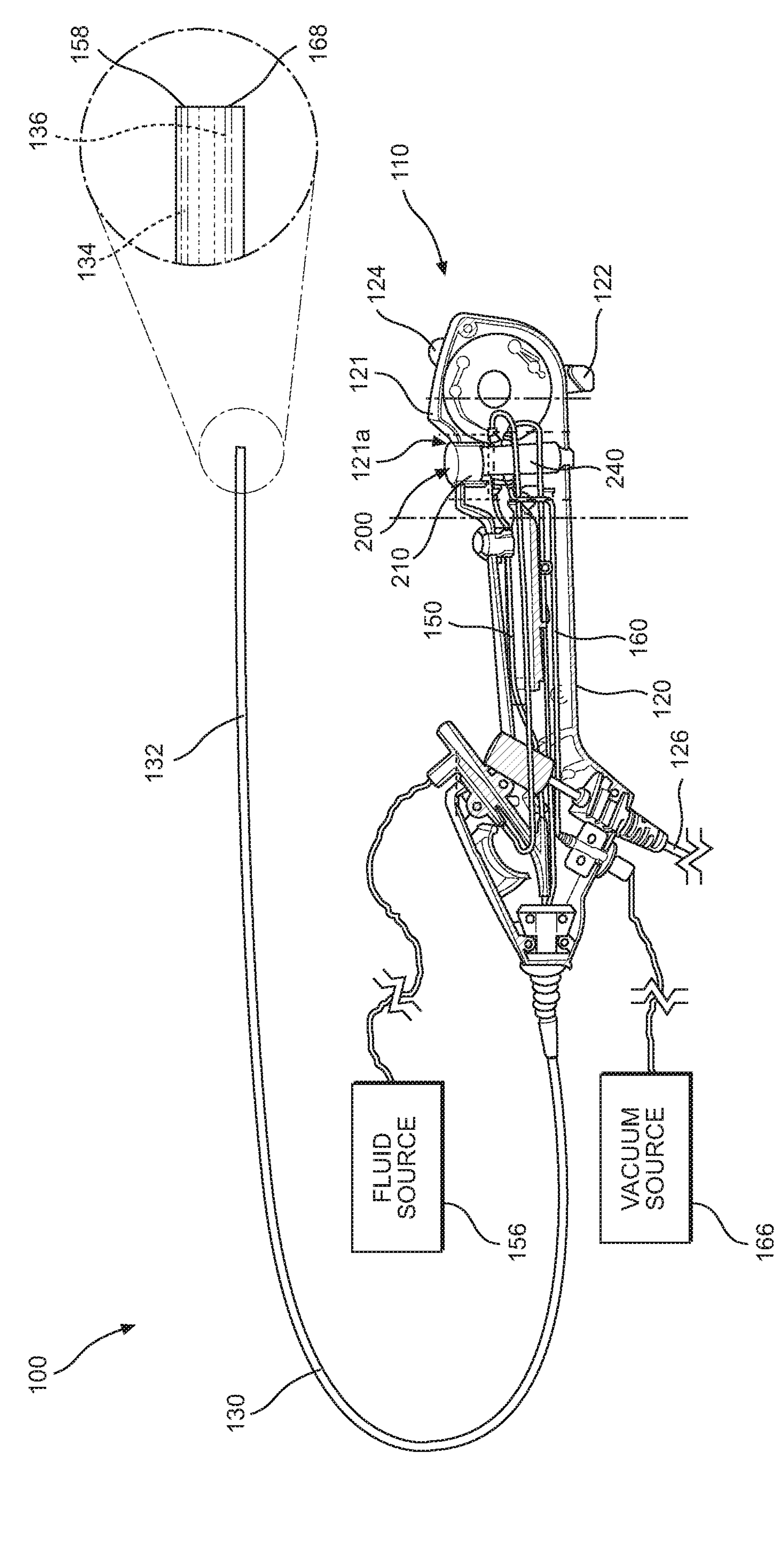
FIG. 1 depicts an exemplary medical system and medical device that includes a valve assembly, according to some aspects of the present disclosure.

Particular aspects of the present disclosure are described in greater detail below. The terms and definitions provided herein control, if in conflict with terms and/or definitions incorporated by reference. The term "distal" refers to a portion farthest away from a user when introducing a device into a subject (e.g., patient). By contrast, the term "proximal" refers to a portion closest to the user when placing the device into the subject. Proximal and distal directions are labeled with arrows marked "P" and "D," respectively, throughout various figures.

As used herein, the terms "comprises," "comprising," "including," "includes," "having," "has," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." Relative terms such as "about," "substantially," and "approximately," etc., are used to indicate a possible variation of ±10% of the stated numeric value or range.

Although scopes including ureteroscopes are referenced herein for illustration purposes, it will be appreciated that the disclosure encompasses any suitable medical device configured to allow an operator to access and view internal body anatomy of a subject and/or to deliver medical instruments, such as, for example, biopsy forceps, graspers, baskets, snares, probes, scissors, retrieval devices, lasers, and other tools, into the subject's body. The medical devices herein may be inserted into a variety of body lumens and/or cavities, such as, for example, the urinary tract or gastrointestinal tract. It will be appreciated that, unless otherwise specified, bronchoscopes, duodenoscopes, endoscopes, gastroscopes, endoscopic ultrasonography ("EUS") scopes, colonoscopes, ureteroscopes, bronchoscopes, laparoscopes, cystoscopes, aspiration scopes, sheaths, catheters, or any other suitable delivery device or medical device may be used in connection with the features described herein.

The medical systems described in this disclosure may include a medical device (e.g., ureteroscope or endoscope). The medical device may include a handle and a shaft extending from a distal end of the handle. The medical device includes one or more channels configured to deliver fluid or provide suction at a distal portion of the shaft. For example, the shaft may include a fluid channel and a suction channel, e.g., each extending from a proximal end of the shaft to respective distal openings at or proximate the distal end of the shaft. The handle may include two conduits in communication with the two respective channels of the shaft.

The medical device includes a valve assembly coupled to the conduits of the handle and configured to exchange fluid and vacuum provided to the channels of the shaft. The valve assembly may include an outer body and an inner body that is movable, e.g., slidable or rotatable, within the outer body. The outer body may include a first fluidics channel, a second fluidics channel, a third fluidics channel, and a fourth fluidics channel. Moving the inner body relative to the outer body may transition the valve assembly between first and second configurations to exchange flow paths between the two conduits of the handle and the two channels of the shaft, such that a user may selectively employ suction through the fluid channel of the shaft and/or fluid through the suction channel of the shaft without adjusting connections between the medical device and sources of fluid and vacuum.

In at least one example, the valve assembly has a first configuration in which the fluidics channel and the second fluidics channel are in fluid communication with each other and with a first conduit of the handle, and the third fluidics channel and the fourth fluidics channel are in fluid communication with each other and with a second conduit of the handle. Further, in a second configuration of the valve assembly, the first fluidics channel and the third fluidics channel are in fluid communication with each other and with the first conduit, and the second fluidics channel and the fourth fluidics channel are in fluid communication with each other and with the second conduit.

For example, in the first configuration, a fluid may flow from a fluid source through a first conduit of the handle to the first fluidics channel and the second fluidics channel, and negative pressure may be provided via a vacuum source through a second conduit of the handle to the third fluidics channel and the fourth fluidics channel. In the second configuration, fluid may flow from the fluid source through the first conduct to first fluidics channel and the third fluidics channel, and negative pressure may be provided through the second conduit to the second fluidics channel and the fourth fluidics channel.

Reference will now be made in detail to examples of the present disclosure described above and illustrated in the accompanying drawings. Wherever possible, reference numbers will be used throughout the drawings to refer to the same or like parts.

FIG. 1 depicts an exemplary medical system 100 according to the present disclosure. Medical system 100 includes a medical device 110 (e.g., a scope such as, a ureteroscope or an endoscope). Medical device 110 includes a handle 120 and a shaft 130. Shaft 130 extends distally from a distal end of handle 120. Shaft 130 may include a distal portion 132 configured to be inserted into a target site (e.g., an interior of a kidney). Shaft 130 may include one or more channels extending from a proximal end of shaft 130 to a distal end of shaft 130. Each of the one or more channels of shaft 130 may include an opening at distal portion 132 (e.g., at a distal face at the distal end of shaft 130). In some examples, the one or more channels of shaft 130 includes a fluid channel 134 having a distal opening 158 at the distal end of the shaft 130 and a suction channel 136 having a distal opening 168 at the distal end of shaft 130. Medical device 110 also includes a valve assembly 200 configured to control the flow direction of fluid and suction through the handle 120. Shaft 130 may include one or more imaging devices (e.g., one or more cameras), illuminating devices (e.g., one or more lights), and/or one or more sensors. Handle 120 (e.g., a proximal portion of handle 120) may include one or more actuators, such actuators 122, 124, configured to deflect/articulate distal portion 132 of shaft 130 and/or control electronic components. An umbilicus 126 coupled to handle 120 may provide electrical/electronic power to medical device 110.

Handle 120 may include two conduits 150, 160 configured to connect to sources of fluid and vacuum, respectively. For example, medical system 100 may include a fluid source 156 and a vacuum source 166. A first end of fluid conduit 150 may include or be connected to a port (e.g., a fluid port or fluid inlet) of handle 120 and a second end of fluid conduit 150 may be connected to valve assembly 200. A first end of suction conduit 160 may include or be connected to a port of the handle (e.g., an aspiration port or aspiration outlet) and the second end of suction conduit 160 may be connected to valve assembly 200. Fluid source 156 and vacuum source 166 may be in fluid communication with valve assembly 200.

Valve assembly 200 may include an outer body 240 and an inner body 210 movable (e.g., slidable or rotatable) relative to outer body 240. A portion of inner body 210 may extend through an aperture 121*a* defined through a housing 121 of handle 120 to receive user input. Outer body 240 of valve assembly 200 includes a plurality of fluidics channels (see, e.g., FIGS. 3A-3C, 4A-4D, 5A-5D, and 6A-6B) configured to deliver fluid or provide suction through handle to shaft 130 via separate passageways. For example, outer body 240 may include four fluidics channels, wherein two of the fluidics channels serve as inlets (one fluid inlet and one aspiration inlet) and two of the fluidics channels serve as outlets (one fluid outlet and one aspiration outlet).

Figure 2A:
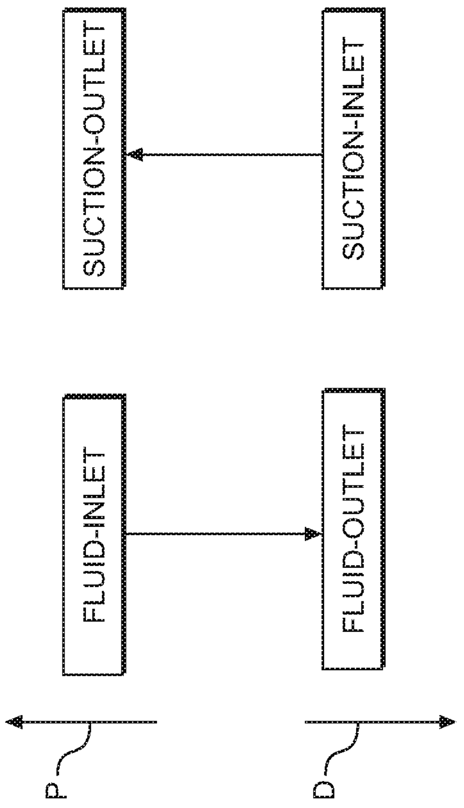
FIGS. 2A-2B show schematics of first and second configurations of a valve assembly, according to some aspects of the present disclosure.
Figure 2B:
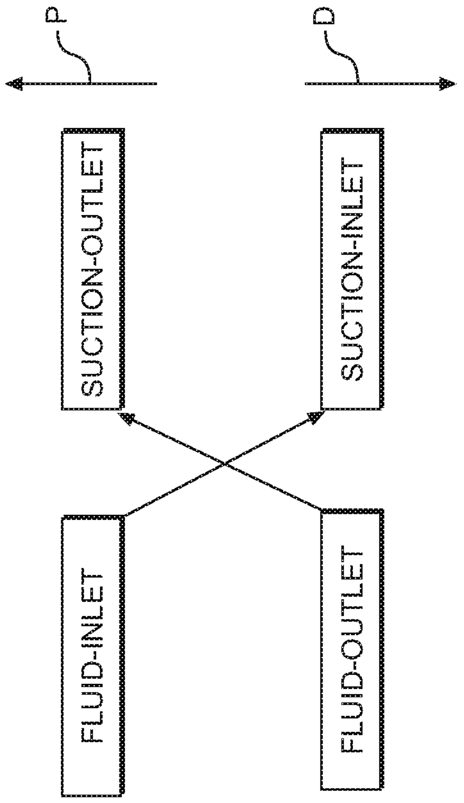

As illustrated schematically in FIGS. 2A and 2B, valve assemblies of the present disclosure may have a first configuration (see FIG. 2A) and a second configuration (see FIG. 2B) that alter flow paths through the valve assembly so that fluid may be provided through different channels of the medical device. In the first configuration, a fluid (e.g., an irrigation fluid) may flow from a fluid source (e.g., fluid source 156) through a first fluidics channel and a second fluidics channel to exit at a fluid outlet (e.g., distal opening 158); while a vacuum source (e.g., vacuum source 166) may provide negative pressure through an aspiration inlet (e.g., distal opening 168), through a fourth fluidics channel and a third fluidics channel. A fluid port or fluid inlet of the handle may be connected to the first fluidics channel in both the first configuration and the second configuration, and the aspiration port or aspiration outlet may be connected to the fourth fluidics channel in both the first configuration and the second configuration of the valve assembly. Thus, a user need not disrupt connections between the fluid source and the valve assembly or between a vacuum source and the valve assembly to switch fluid and suction provided to the shaft.

Referring again to FIG. 1, in the first configuration of valve assembly 200, material pulled through suction channel 136 may form a blockage in shaft 130 and/or handle 120. A user may remove the blockage by transitioning valve assembly 200 from the first configuration to the second configuration such that fluid flows through the suction channel to remove the blockage.

For example, in the second configuration, a fluid (e.g., an irrigation fluid) may flow from fluid source 156 through the first fluidics channel into the fourth fluidics channel to exit at distal opening 168. That is, instead of flowing from the first fluidics channel to the second fluidics channel, the fluid may flow from the first fluidics channel to the fourth fluidics channel.

Figure 3A:
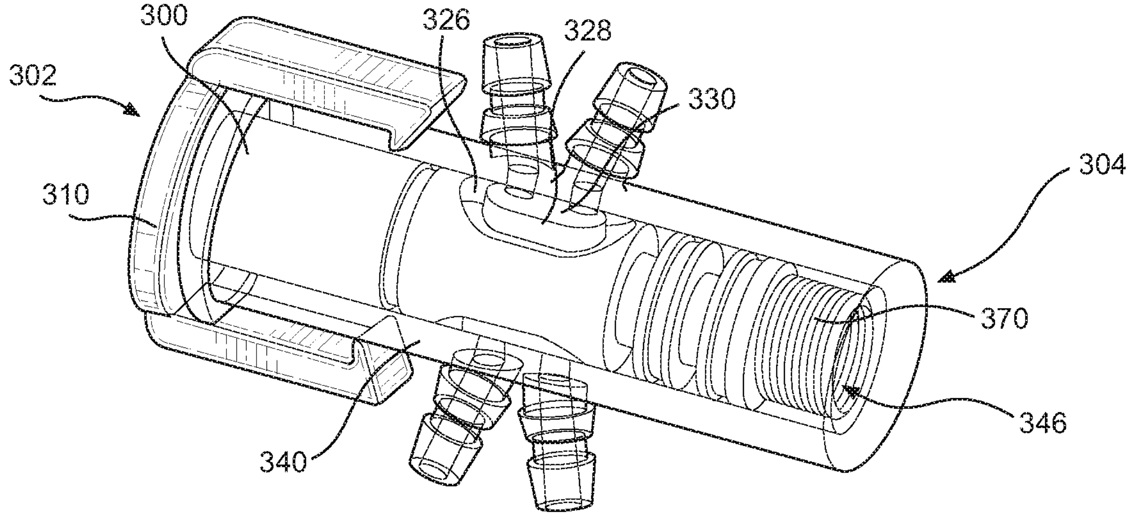
FIGS. 3A-3C depict an exemplary valve assembly according to some aspects of the present disclosure in a first configuration (FIG. 3B) and a second configuration (FIGS. 3A and 3C).
Figure 3B:
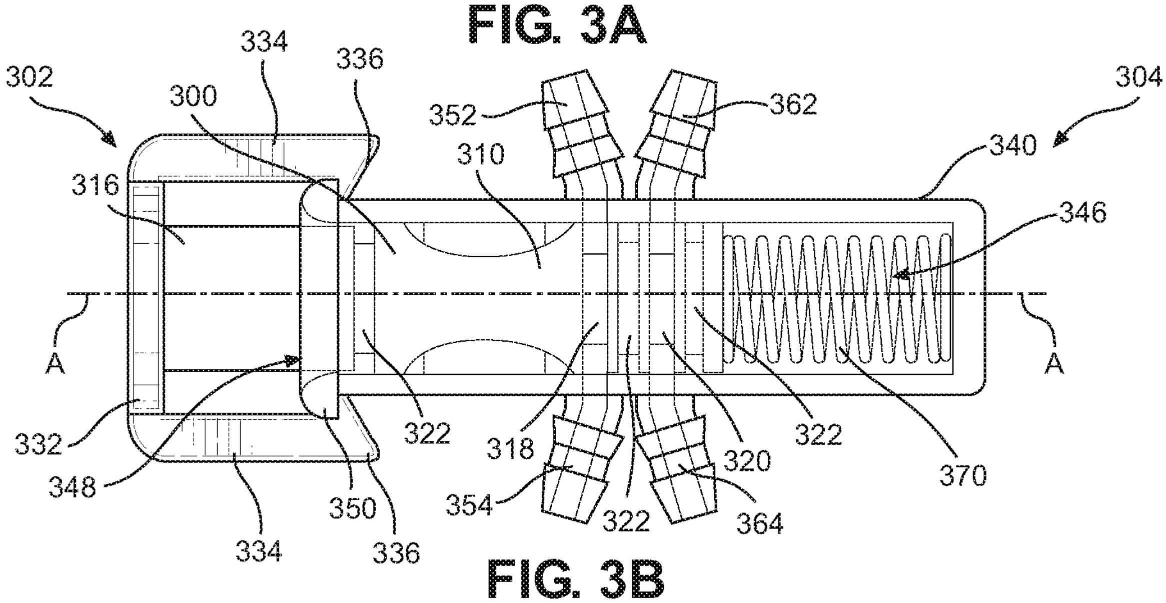
Figure 3C:
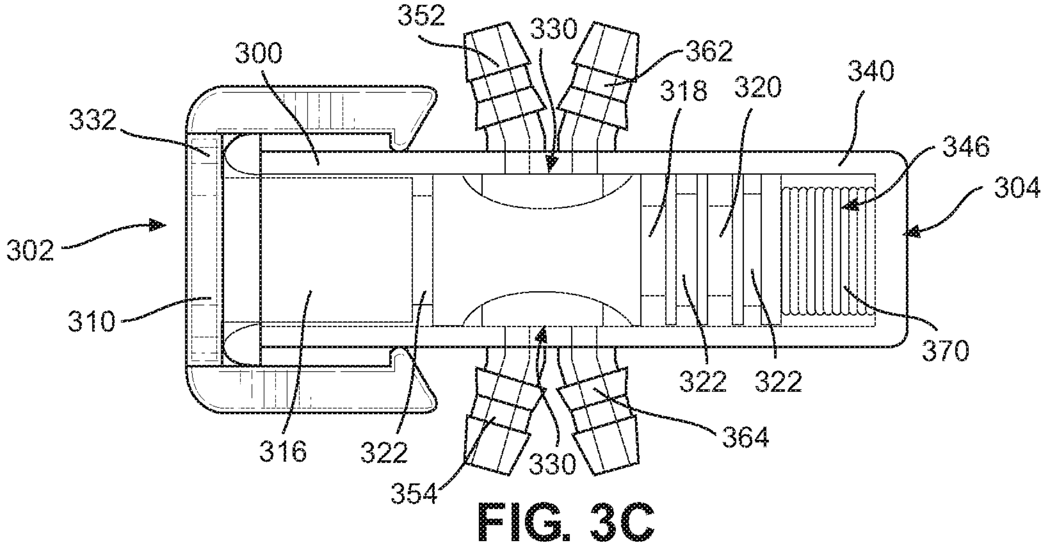

FIGS. 3A-3C depict an exemplary valve assembly 300. Valve assembly 300 may in connection to medical system 100 and/or medical device 110, e.g., medical device 110 may include valve assembly 300 instead of valve assembly 200. Valve assembly 300 includes a first end 302 and a second end 304. Valve assembly 300 may define a central longitudinal axis A. Valve assembly 300 includes an inner body 310 and an outer body 340. Inner body 310 may be movable, e.g., slidable, relative to outer body 340. Valve assembly 300 may include a first configuration (FIG. 3B) and a second configuration (FIG. 3C). Sliding inner body 310 relative to outer body 340 may transition valve assembly 300 between the first configuration and the second configuration. For example, valve assembly 300 is shown transitioning from the first configuration (FIG. 3B) to the second configuration (FIG. 3C) as inner body 310 slides toward second end 304.

Outer body 340 may be coaxial with and extend along central longitudinal axis A. Outer body 340 is illustrated as having a cylindrical shape, however other shapes are possible and contemplated herein. Outer body 340 may define a chamber 346 having an opening 348 at first end 302. Chamber 346 and opening 348 may each be sized and shaped to receive at least a portion of inner body 310 therein. Chamber 346 and opening 348 may be coaxial with central axis A. At first end 302, chamber 346 may include a flange 350 extending radially outward from an exterior surface of outer body 340. Flange 350 may be configured to limit movement of inner body 310 relative to outer body 340.

As shown in FIGS. 3B and 3C, outer body 340 may include a plurality of fluidics channels including a first fluidics channel 352, a second fluidics channel 354, a third fluidics channel 362, and a fourth fluidics channel 364. First fluidics channel 352 and third fluidics channel 362 may be adjacent to each other on a first side of outer body 340. Second fluidics channel 354 and fourth fluidics channel 364 may be adjacent to each other on a second side of outer body 340, opposite to the first side.

Inner body 310 may include a first portion 316 and a second portion 332. Inner body 310 may extend along and be coaxial with central axis A. First portion 316 may extend from second portion 332 and be slidably received within chamber 346 and opening 348. For example, first portion 316 may extend toward second end 304. In the first configuration of valve assembly 300, a portion of first portion 316 be received within chamber 346 and opening 348 and another portion of first portion 316 may extend beyond opening 348 away from chamber 346.

Inner body 310 may include a first end connected to second portion 332 and a second end. First portion 316 may include two channels 318, 320. Channels 318, 320 may extend radially inward from an exterior surface of first portion 316 along a perimeter or circumference of a lateral cross section of first portion 316. For example, as shown in FIGS. 3A-3C, channels 318, 320 may include an annular shape and may radially surround central axis A along the circumference of first portion 316. First portion 316 may include two or more cavities 326 extending radially inward from the exterior surface of first portion 316 toward central axis A. Cavities 326 may be at opposite positions along the perimeter or circumference of first portion 316. For example, as shown in FIG. 3A, first portion 316 may include two cavities 326 circumferentially opposite to one another. Cavities 326 may be aligned along a length of first portion 316. Cavities 326 may each include a protrusion 328 extending radially outward from a surface of cavity 326. Each protrusion 328 may extend radially outward and terminate at or before the perimeter or circumference of first portion 316. Each protrusion may include a basin or cavity 330 extending radially inward toward central axis A. For example, cavity 330 may extend radially inward from a radially outward most surface of protrusion 328. First portion 316 may include one or more sealing channels 322. Similar to channels 318, 320, sealing channels 322 may extend radially inward from an exterior surface of first portion 316 along the perimeter or circumference of first portion 316. For example, as shown in FIG. 3B, channels 322 may include an annular shape and may radially surround central axis A along the circumference of first portion 316. Sealing channels 322 may be configured to fluidly isolate channel 318 from channel 320 and fluidly isolate cavities 330 from one or more of channels 318, 320. Sealing channels 322 may be configured to receive an O-ring therein to facilitate fluid isolation. As shown in FIG. 3B, first portion 316 may include three sealing channels. Cavities 330, channel 318, channel 320, and sealing channels 322 may be arranged along the length of first portion 316. As an example, sealing channels 322 may include a staggered configuration with channels 318, 320 and cavities 330.

Second portion 332 may include a circular disk shape. A dimension (e.g., a diameter or width) of second portion 332 may be greater than a dimension (e.g., a diameter or width) of opening 348 and flange 350 such that second portion 332 is not receivable within chamber 346 or opening 348 and second portion 332 may contact flange 350 as inner body 310 slides toward second end 304. Second portion 332 may include one or more protrusions 334 extending parallel with the central axis toward second end 304. For example, as shown in FIG. 3C, one or more protrusions 334 may include two protrusions 334. Protrusion(s) 334 may extend from a circumference or perimeter of second portion 332. An end of protrusion(s) 334 extending toward second end 304 may include a projection 336. Projections 336 may extend radially inward toward central axis A. Projections 336 may be positioned nearer second end 304 than flange 350. Projections 336 may snap-fit with flange 350. For example, as shown in FIG. 3B, a planar surface of each projection 336 may contact a planar surface of flange 350 to prevent inner body 310 from decoupling from outer body 340.

As mentioned above, valve assembly 300 includes a first configuration (FIG. 3B) and a second configuration (FIG. 3C). As shown in FIG. 3B, in the first configuration, inner body 310 may be positioned relative to outer body 340 such that (i) channel 318 is aligned with and in fluid communication with first fluidics channel 352 and second fluidics channel 354 and (ii) channel 320 is aligned with and in fluid communication with third fluidics channel 362 and fourth fluidics channel 364. Channel 318 and fluidics channels 352, 354 may be fluidly isolated from channel 320 and fluidics channels 362, 364.

In an exemplary use in connection to medical system 100, fluid may flow from fluid source 156 via fluid conduit 150 through first fluidics channel 352, channel 318, and second fluidics channel 354, and exit at an opening (e.g., distal opening 158) at the distal end of shaft 130. Vacuum source 166 may be in fluid communication via suction conduit 160 with fourth fluidics channel 364 such that fluid or material at the target site are pulled through an opening (e.g., distal opening 168) at the distal end of shaft 130 and flow through third fluidics channel 362, channel 320, and fourth fluidics channel 364 toward and/or into vacuum source 166. Further, in the first configuration, projection(s) 336 may contact flange 350 to prevent decoupling of inner body 310 and outer body 340.

A user may transition valve assembly 300 from the first configuration to the second configuration by sliding inner body 310 relative to outer body 340, e.g., pressing an end of inner body 310. For example, the end of inner body 310 may be accessible to the user on handle 120 so that the user can press inner body 310 relative to the housing of handle 120. As shown in FIG. 3C, in the second configuration, inner body 310 may be positioned relative to outer body 340 such that (i) first fluidics channel 352, third fluidics channel 362, and one cavity 330 are in fluid communication and (ii) second fluidics channel 354, another, different cavity 330 are in fluid communication. Fluid may flow from fluid source 156 via fluid conduit 150 through first fluidics channel 352, cavity 330, and third fluidics channel 362, and exit at distal opening 168. Vacuum source 166 may be in fluid communication with fourth fluidics channel 364 via suction conduit 160 such that fluid or material at the target site are pulled through distal opening 168 and flow through second fluidics channel 354, cavity 330, and fourth fluidics channel 364 toward and/or into vacuum source 166.

As mentioned above, valve assembly 300 may be positioned within handle 120 such that an end of inner body 310 (e.g., at least a portion of second portion 332) extends through aperture 121*a* defined through housing 121 of handle 120. The end of inner body 310 may be an actuator of handle 120. To transition valve assembly 300 from the first configuration to the second configuration, the user may press the exposed portion of inner body 310 such that inner body 310 slides within outer body 340 until it reaches the second configuration. Optionally, valve assembly 300 may include a biasing element 370 (e.g., a spring) configured to bias inner body 310 toward first end 302 and to automatically transition valve assembly 300 from the second configuration to the first configuration when the exposed portion of inner body 310 is no longer being pressed by the user. Biasing element 370 may be within chamber 346.

Figure 4A:
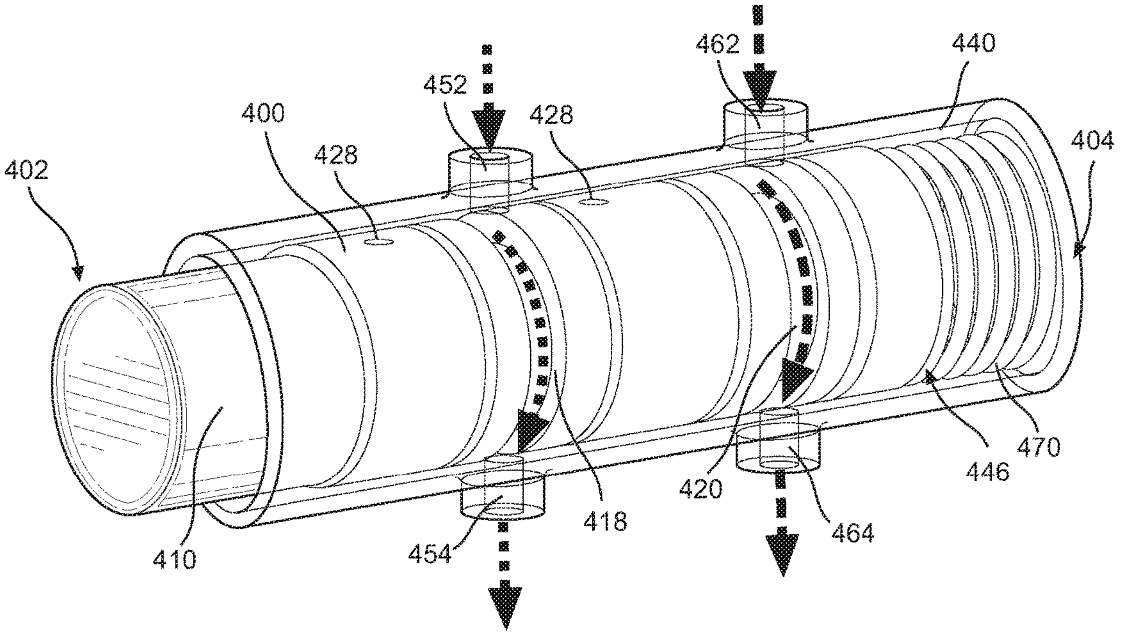
FIGS. 4A-4D depict another exemplary valve assembly according to some aspects of the present disclosure.
Figure 4B:
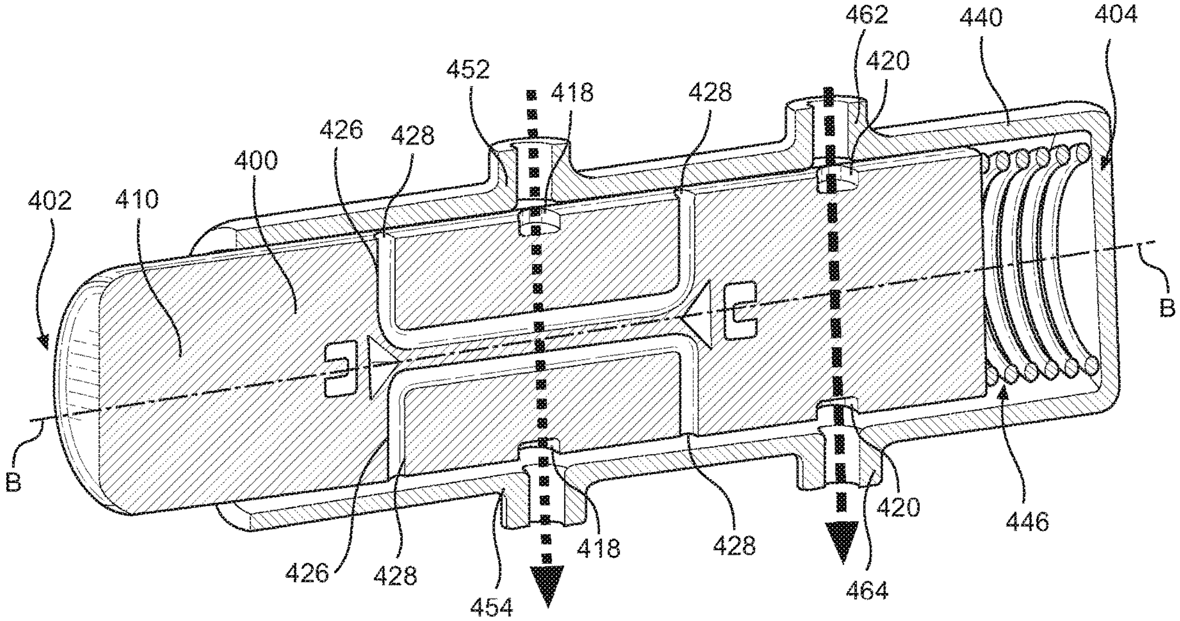
Figure 4C:
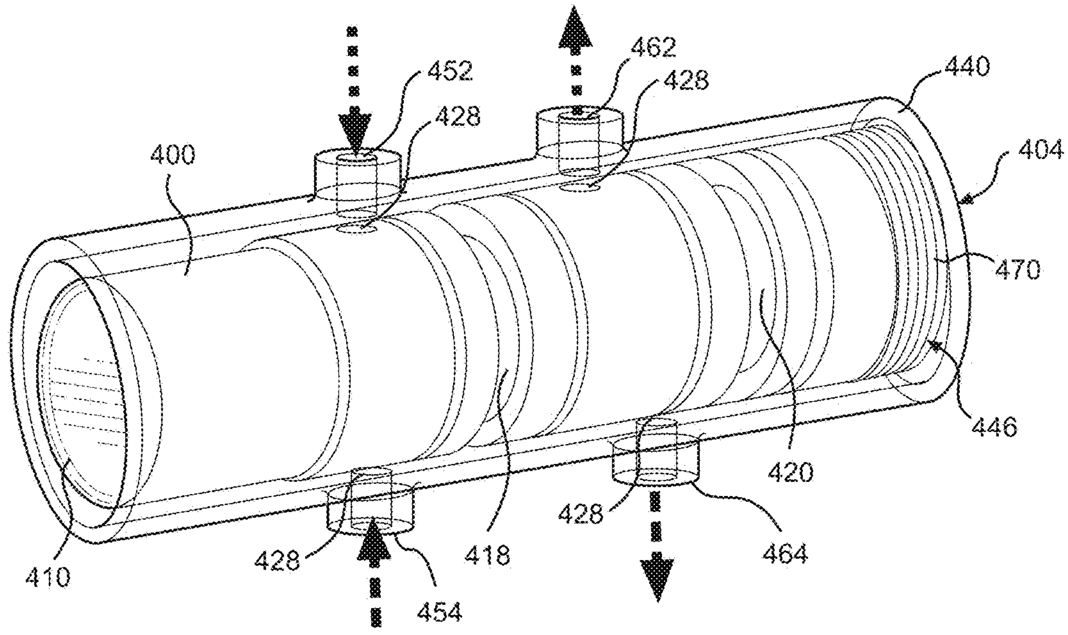
Figure 4D:
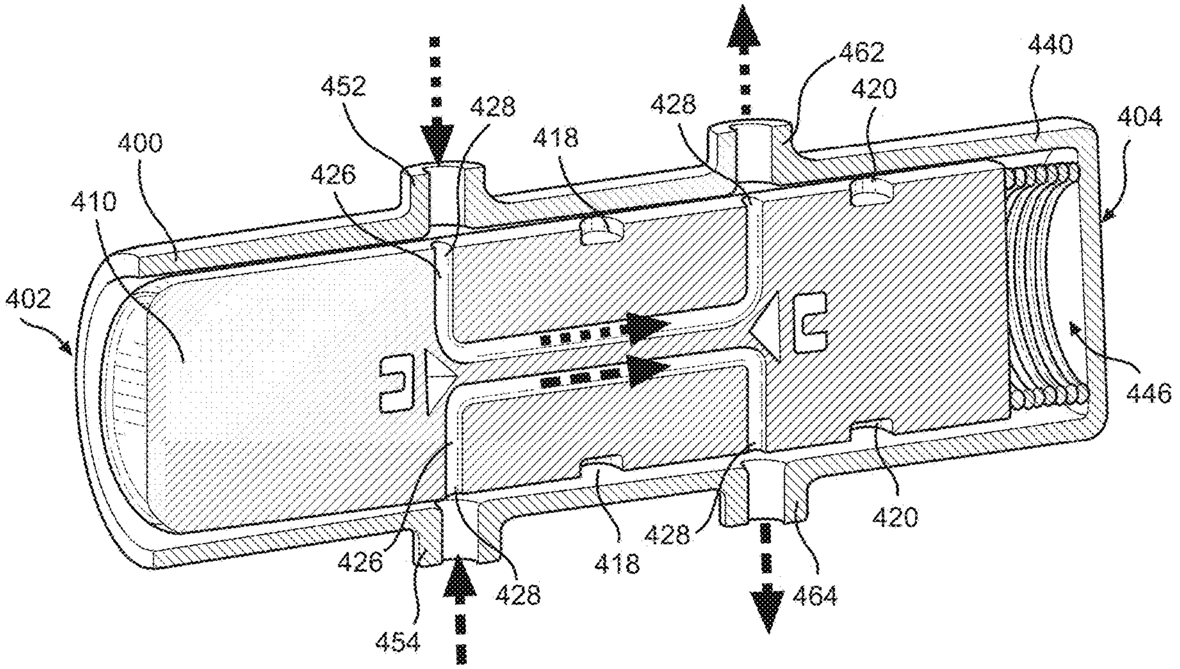

FIGS. 4A-4D depict another exemplary valve assembly 400 that may be used with any of the features of medical system 100 and/or medical device 110. Further, valve assembly 400 may include any of the features of valve assembly 300 unless otherwise specified. Valve assembly 400 may define a central longitudinal axis B. Valve assembly 400 includes an inner body 410 and an outer body 440. Inner body 410 may be movable, e.g., slidable, relative to outer body 440. Valve assembly 400 may include a first configuration (FIGS. 4A-4B) and a second configuration (FIG. 4C-4D). Sliding inner body 410 relative to outer body 440 may transition valve assembly 400 between the first configuration and the second configuration. Optionally, valve assembly 400 may include a biasing element, e.g., a spring, which biases the position of inner body 410 relative to outer body 440. For example, a chamber 446 of outer body 440 may include a biasing element 470 configured to bias valve assembly 400 in the first configuration, e.g., to return valve assembly 400 to the first configuration from the second configuration.

Outer body 440 may include a plurality of fluidics channels including a first fluidics channel 452, a second fluidics channel 454, a third fluidics channel 462, and a fourth fluidics channel 464. Inner body 410 may include lumens, e.g., first lumens 418, 420. At least a portion or an entirety of first lumens 418, 420 may be parallel to each other. In use in connection to medical device 110, one of first lumens 418, 420 may be in fluid communication with fluid conduit 150 and the other of first lumens 418, 420 may be in fluid communication with suction conduit 160.

Inner body 410 may include second lumens, e.g., two U-shaped lumens 426 positioned circumferentially opposite one another. Portions of second lumens 426 may be parallel to each other and perpendicular or otherwise transverse to first lumens 418, 420. In use in connection to medical device 110, one of second lumens 426 may be in fluid communication with fluid conduit 150 and the other of second lumens 426 may be in fluid communication with suction conduit 160. The first lumens 418, 420 and second lumens 426 may have a staggered configuration as shown in FIGS. 4A-4D, e.g., at least a portion of second lumens 426 being between the first lumens 418, 420. For example, second lumens 426 may include openings 428 at an exterior surface of inner body 410. One opening 428 of each second lumen 426 may be positioned nearer a first end 402 than lumen 418 and the other opening of each second lumen 426 may be positioned between first lumens 418, 420. In the second configuration of valve assembly 400, openings 428 of each lumen may be aligned with one of fluidics channels 452, 454, 462, 464. For example, openings 428 of one first lumen 426 may be aligned with first fluidics channel 452 and third fluidics channel 462, and openings 428 of the other first lumen 426 may be aligned with second fluidics channel 454 and fourth fluidics channel 464.

In an exemplary use wherein medical device 110 includes valve assembly 400, fluid may flow from fluid source 156 through first fluidics channel 452, first lumen 426, and third fluidics channel 462, and exit at distal opening 168. Vacuum source 166 may be in fluid communication with fourth fluidics channel 464 such that fluid or material at the target site are pulled through distal opening 168 and flow through second fluidics channel 454, second lumen 426, and fourth fluidics channel 464 toward and/or into vacuum source 166.

Figure 5B:
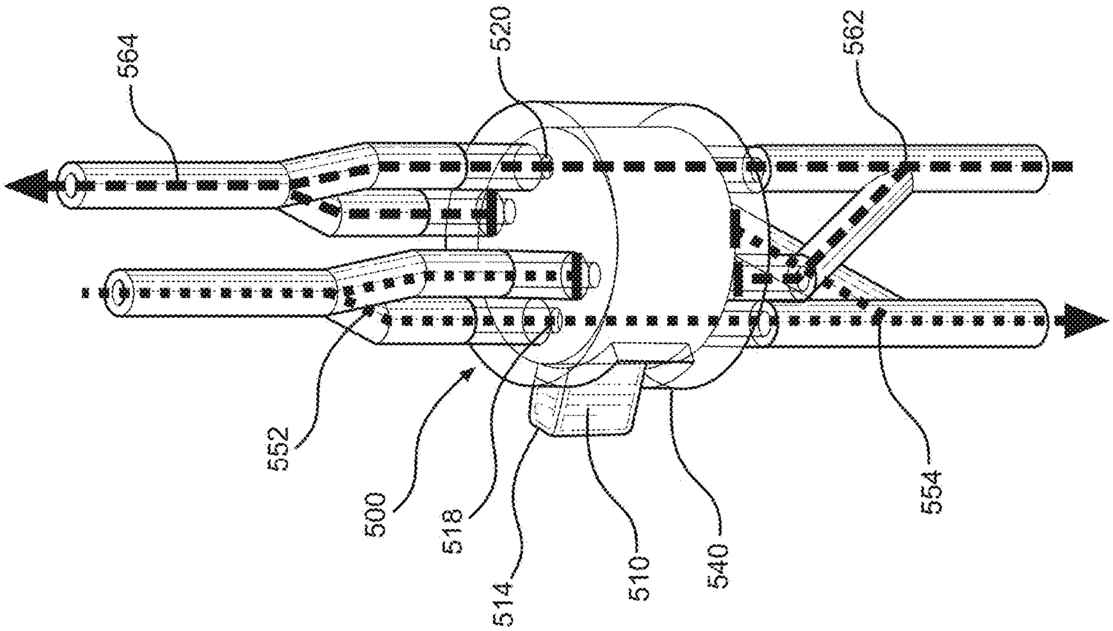
FIGS. 5A-5D depict another exemplary valve assembly according to some aspects of the present disclosure.
Figure 5A:
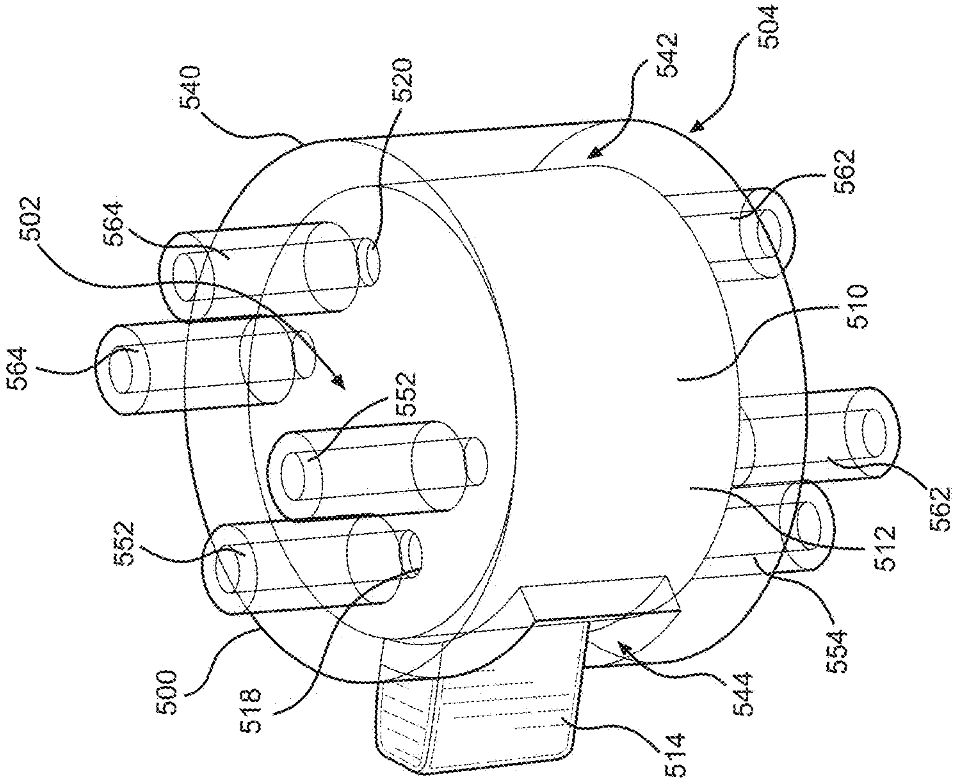
Figure 5D:
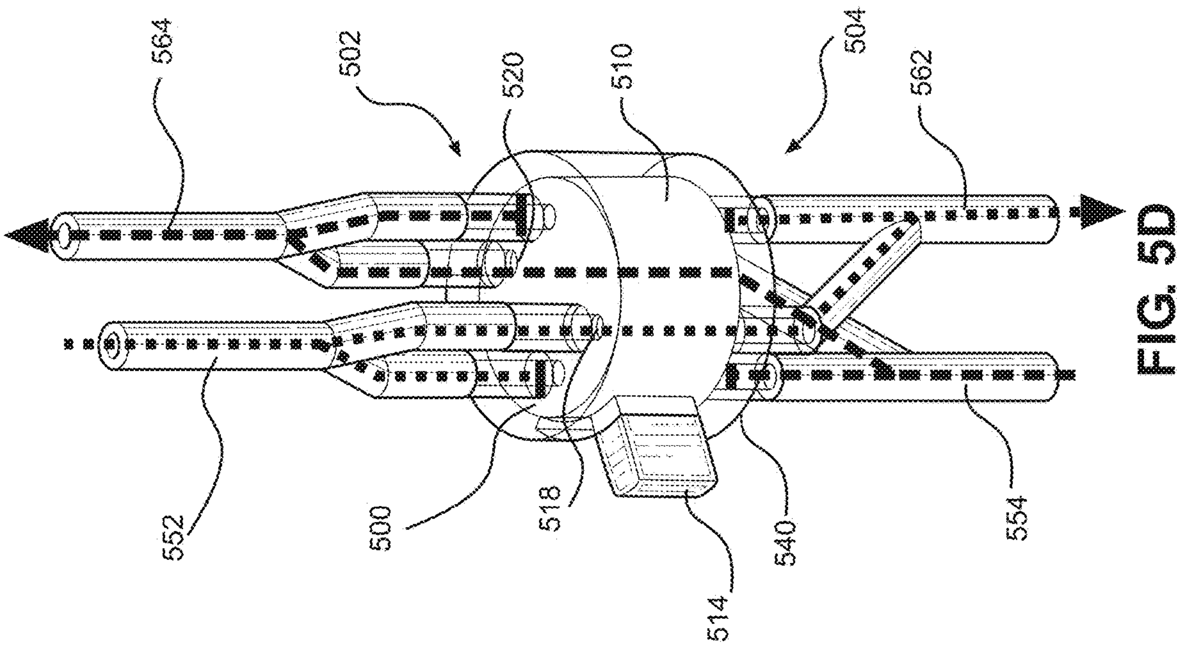
Figure 5C:
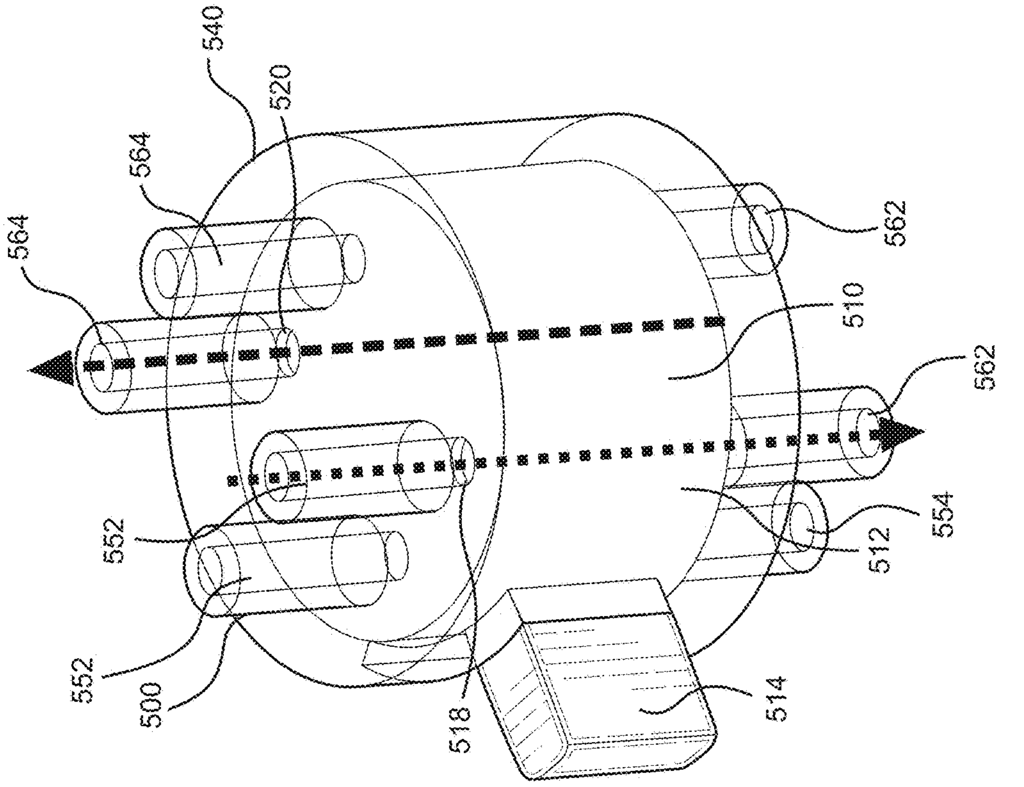

FIGS. 5A-5D depict another exemplary valve assembly 500. Valve assembly 500 may include any of the features of valve assembly 300 or 400, and may be used in connection to medical device 110 (e.g., in place of valve assembly 200). Valve assembly 500 includes a first end 502 and a second end 504. Valve assembly 500 includes an inner body 510 and an outer body 540. Inner body 510 may be movable, e.g., rotatable, relative to outer body 540. Valve assembly 500 may include a first configuration (FIG. 5A-5B) and a second configuration (FIG. 5C-5D). Rotating inner body 510 relative to outer body 540 may transition valve assembly 500 between the first configuration and the second configuration.

As depicted in FIGS. 5A and 5C, inner body 510 may include a first portion 512 and an end 514 extending outside first portion 512. First portion 512 may include a cylindrical shape. First portion 512 may include a first lumen 518 and a second lumen 520. Lumens 518, 520 may include corresponding openings in first portion 512. End 514 may extend from a curved surface of first portion 512. First portion 512 may include a central axis and may be rotated about the central axis within outer body 540, e.g., by user input received at end 514 of inner body 510 that is accessible to the user.

Outer body 540 may include a cylindrical shape but other shapes are possible. A central axis of outer body 540 may be coaxial and parallel with the central axis of first portion 512. Outer body 540 may include a first side at first end 502 and a second side at second end 504. The first side and the second side of outer body 540 may include a circular shape. Outer body 540 may include a chamber 542 sized and shaped to contain at least a portion of inner body 510. For example, chamber 542 may be sized and shaped to contain first portion 512. Outer body 540 may include an opening 544 defined through a wall of outer body 540. For example, opening 544 may be defined through a curved wall of outer body 540. End of inner body 510 may extend through opening 544. Rotating end 514 relative to outer body 540 may transition valve assembly 500 between the first configuration and the second configuration.

As shown in FIGS. 5B and 5D, outer body 540 may include a plurality of fluidics channels including a first fluidics channel 552, a second fluidics channel 554, a third fluidics channel 562, and a fourth fluidics channel 564. Each of fluidics channels 552, 554, 562, 564 may split into two pathways (e.g., tubes) forming a Y-connection.

As shown in FIG. 5A, the first side of outer body 540 may include the Y-pathways of first fluidic channel 552 and fourth fluidic channel 564, and the second side of outer body 540 may include the Y-pathways of second fluidic channel 554 and third fluidic channel 562. Outer body 540 may include apertures on each side and in communication with chamber 542 for each pathway of the fluidics channels. In each configuration of valve assembly 500, one pathway of each fluidics channel 552, 554, 562, 564 may be in fluid communication with one of lumens 518, 520 and the other pathway of each fluidics channel 552, 554, 562, 564 may terminate at a surface of first portion 512 of inner body 510. Thus, fluid communication may be provided flow through one pathway with the other pathway blocked.

As shown in FIGS. 5A-5B, in the first configuration, inner body 510 may be rotationally positioned relative to outer body 540 such that (i) lumen 518 is aligned with and in fluid communication with a first pathway of first fluidics channel 552 and a first pathway of second fluidics channel 554 and (ii) lumen 520 is aligned with and in fluid communication with a first pathway of third fluidics channel 562 and a first pathway of fourth fluidics channel 564. For example, end 514 of inner body 510 may be at the first end of opening 544. Lumen 518 and fluidics channels 552, 554 may be fluidly isolated from lumen 520 and fluidics channels 562, 564.

In an exemplary use in connection with medical system 100 and medical device 110 (wherein valve assembly 500 is used in place of valve assembly 200), fluid may flow from fluid source 156 via fluid conduit 150 through first fluidics channel 552, lumen 518, second fluidics channel 554, fluid channel 134 and exit at an opening (e.g., distal opening 158) at the distal end of shaft 130. Vacuum source 166 may be in fluid communication via suction conduit 160 with fourth fluidics channel 564 such that fluid or material at the target site are pulled through an opening (e.g., distal opening 168) at the distal end of shaft 130 and flow through suction channel 136, third fluidics channel 562, lumen 520, and fourth fluidics channel 564 toward and/or into vacuum source 166. Further, in the first configuration, a second pathway of each of fluidic channels 552, 554, 562, 564 may terminate at a dead end (e.g., at the planar surface of inner body 510.)

As shown in FIGS. 5C-5D, in the second configuration, inner body 510 may be rotated to outer body 540 such that (i) the second pathway of first fluidics channel 552, lumen 518, and the second pathway of third fluidics channel 562 are in fluid communication and (ii) the second pathway of second fluidics channel 554, lumen 520, and the second pathway of fourth fluidics channel 564 are in fluid communication. Lumen 518 and fluidics channels 552, 562 may be fluidly isolated from lumen 520 and fluidics channels 554, 564. Fluid may flow from fluid source 156 via fluid conduit 150 through first fluidics channel 552, lumen 518, and third fluidics channel 562, suction channel 136 and exit at distal opening 168. Vacuum source 166 via suction conduit 160 may be in fluid communication with fourth fluidics channel 564 such that fluid or material at the target site are pulled through distal opening 158 and flow through fluid channel 134, second fluidics channel 554, lumen 520, and fourth fluidics channel 564 toward and/or into vacuum source 166. Further, in the second configuration, a first pathway of each of fluidic channels 552, 554, 562, 564 may terminate at a dead end (e.g., at the planar surface of inner body 510.)

Valve assembly 500 may be positioned within handle 120 such that end 514 of inner body 510 extends through aperture 121*a* of housing 121 of handle 120. End 514 may be an actuator of handle 120. To transition valve assembly 500 between the first configuration and the second configuration, the user may rotate end 514, e.g., like flipping a switch.

Figure 6A:
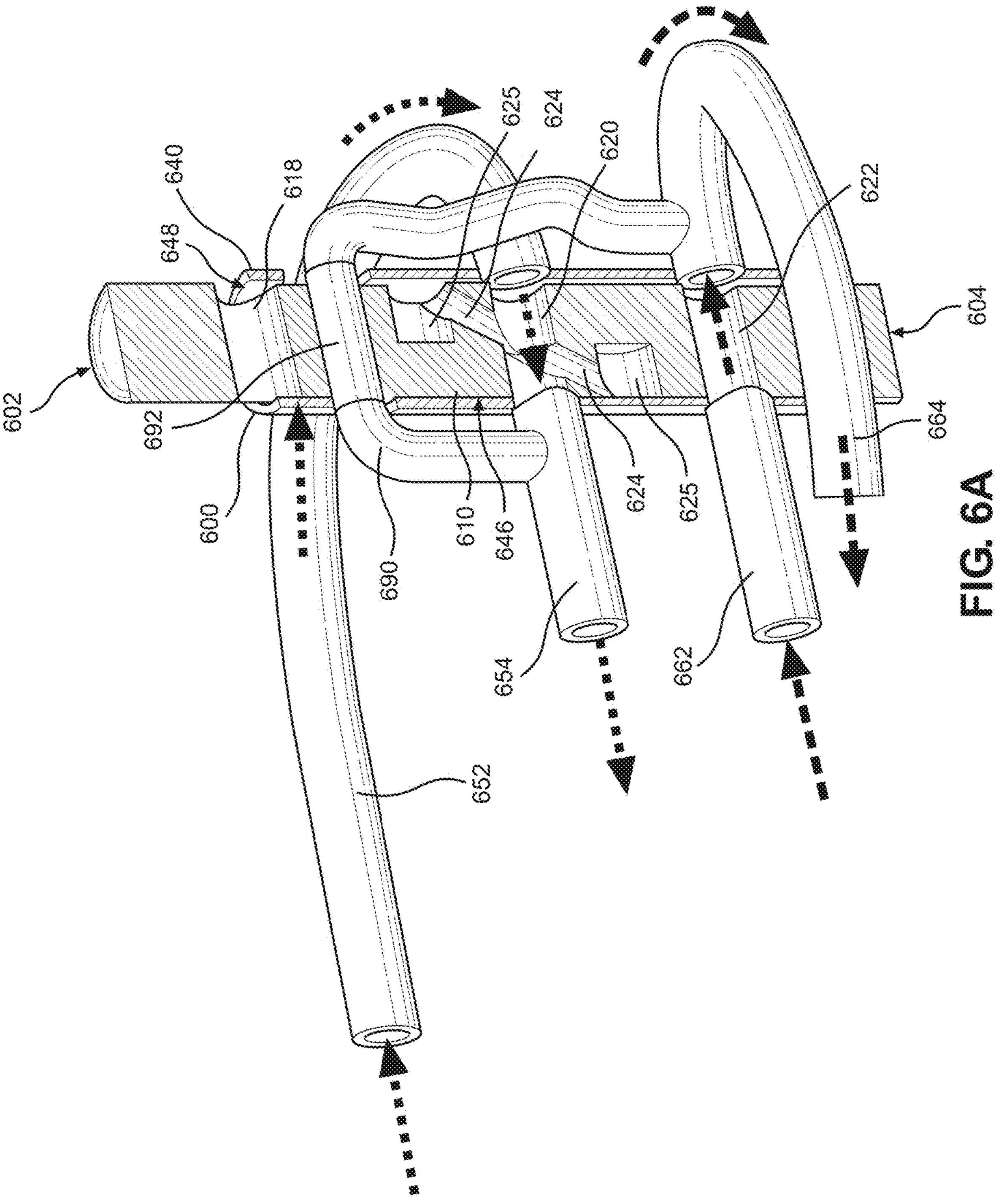
FIGS. 6A-6B depict another exemplary valve assembly according to the present disclosure in a first configuration (FIG. 6A) and a second configuration (FIG. 6B).
Figure 6B:
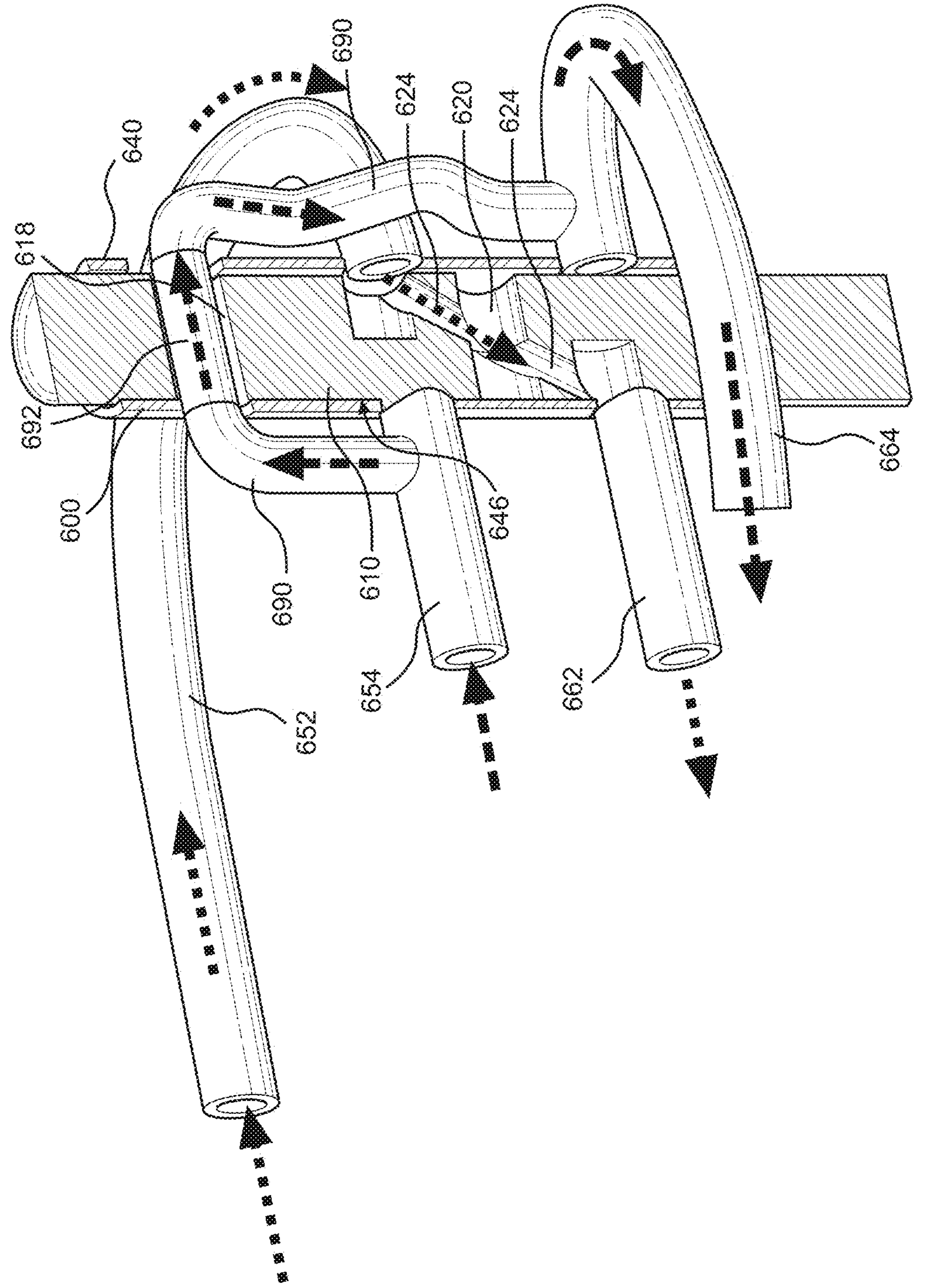

FIGS. 6A-6B depict another exemplary valve assembly 600 according to aspects of the present disclosure. Valve assembly 600 may include any of the features of valve assembly 300, 400, and/or 500 unless otherwise specified, and may be used in connection with medical system 100 and medical device 110 (e.g., in place of valve assembly 200). Valve assembly 600 includes a first end 602 and a second end 604. Valve assembly 600 includes an inner body 610 and an outer body 640. Inner body 610 may be movable, e.g., slidable relative to outer body 640. Valve assembly 600 may include a first configuration (FIG. 6A) and a second configuration (FIG. 6B). Sliding inner body 610 relative to outer body 640 may transition valve assembly 600 between the first configuration and the second configuration.

Inner body 610 may include a cylindrical shape although other shapes are contemplated. Inner body 610 may include one or more lumens. Each lumen may extend through inner body 610 from a first location along a curved surface of inner body 610 to second location along the curved surface of inner body 610. The second location may be circumferentially opposite to the first location. The one or more lumens may include a first lumen 618, a second lumen 620, and a third lumen 622. Lumens 618, 620, 622 may each extend perpendicular or otherwise transverse to a central axis of inner body 610. Optionally, lumens 618, 620, 622 may extend parallel to one another. Lumens 618, 620, 622 may be positioned along inner body 610 such that first lumen 618 is nearest first end 602, third lumen 622 is nearest second end 604, and second lumen 620 is between first lumen 618 and third lumen 622. The one or more lumens may include a fourth lumen 624. Fourth lumen 624 may be transverse to lumens 618, 620, 622. For example, fourth lumen 624 may extend from a first location to a second location, the first location being nearer to first end 602 than the second location. Relative to the central axis of inner body 610, a distance between the first location and the second location of fourth lumen 624 may be equal to or approximately equal to a distance between second lumen 620 and third lumen 622. Fourth lumen 624 may intersect second lumen 622. According to some aspects of the present disclosure, fourth lumen 624 may include a cavity 625 at the first location and a cavity 625 at the second location. Cavities 625 may assist a machine in defining (e.g., grinding, milling, drilling, etc.) fourth lumen 624 through inner body 610. According to other aspects, cavities 625 may be omitted.

Optionally, outer body 640 may include a cylindrical shape. Outer body 640 may include a chamber 646 and an opening 648 in communication with chamber 646. Opening 648 may be positioned at first end 602. Opening 648 and chamber 646 may be sized and shaped to receive inner body 610 therein. For example, inner body 610 may be slidable received within opening 648 and chamber 646.

As shown in FIGS. 6A and 6B, outer body 640 may include a plurality of fluidics channels including a first fluidics channel 652, a second fluidics channel 654, a third fluidics channel 662, and a fourth fluidics channel 664. Each of fluidics channels 652, 654, 662, 664 may include a corresponding aperture defined through a wall of outer body 640 and in fluid communication with at least a portion of chamber 646.

Valve assembly 600 may include a connecting tube 690. A first end of connecting tube 690 may be connected to and in fluid communication with second fluidics channel 654 and a second end of connecting tube 690 may connected to and be in fluid communication with fourth fluidics channel 664. Connecting tube 690 may include a pinch portion 692. Pinch portion 692 may be configured to selectively prevent fluid flow through connecting tube 690. For example, in the first configuration (FIG. 6A), pinch portion 692 may prevent fluid flow through connecting tube 690 and, in the second configuration (FIG. 6B), pinch portion 692 may permit fluid flow through connecting tube 690. In the second configuration, pinch portion 692 may be received within lumen 618 and may permit fluid flow through connecting tube 690.

As shown in FIG. 6A, in the first configuration of valve assembly 600, inner body 610 may be slidably positioned relative to outer body 640 such that (i) lumen 620 is aligned with and in fluid communication with first fluidics channel 652 and second fluidics channel 654; and (ii) lumen 622 is aligned with and in fluid communication with third fluidics channel 662 and fourth fluidics channel 664. Pinch portion 692 may prevent, inhibit, or limit fluid flow through connecting tube 690. For example, as shown in FIG. 6A, pinch portion 692 may be in a compressed state. Pinch portion 692 may be compressed (e.g., squeezed or clamped) between inner body 610 and outer body 640. Pinch portion 692 may be compressed between an interior surface of inner body 610 and an interior surface of outer body 640. When pinch portion 692 is compressed, pinch portion 692 may be in the compressed state and may prevent or limit fluid flow through connecting tube 690 into fourth fluidics channel 664. According to some aspects, inner body 610 may include a slot configured to receive pinch portion 692 therein and compress pinch portion 692 between interior walls of the slot. The slot may include an opening configured to receive pinch portion 692 therein and extending towards first end 602 and an end extending toward second end 604. Lumen 620 and fluidics channels 652, 654 may be fluidly isolated from lumen 622 and fluidics channels 662, 664.

In an exemplary use in connection with medical system 100 and medical device 110, fluid may flow from fluid source 156 via fluid conduit 150 through first fluidics channel 652, lumen 620, second fluidics channel 654, and fluid channel 134 and exit at an opening (e.g., distal opening 158) at the distal end of shaft 130. Vacuum source 166 via suction conduit 160 may be in fluid communication with fourth fluidics channel 664 such that fluid or material at the target site are pulled through an opening (e.g., distal opening 168) at the distal end of shaft 130 and flow through suction channel 136, third fluidics channel 662, lumen 622, and fourth fluidics channel 664 toward and/or into vacuum source 166.

As shown in FIG. 6B, in the second configuration, inner body 610 may be slidably positioned relative to outer body 640 such that (i) first fluidics channel 652, fourth lumen 624, and third fluidics channel 662 are in fluid communication; (ii) pinch portion 692 of connecting tube 690 is received within lumen 618 and permits fluid flow through connecting tube 690; and (iii) second fluidics channel 654, connecting tube 690, and fourth fluidics channel 664 are in fluid communication. Fourth lumen 624 and fluidics channels 652, 662 may be fluidly isolated from connecting tube 690 and fluidics channels 654, 664. Fluid may flow from fluid source 156 via fluid conduit 150 through first fluidics channel 652, fourth lumen 624, third fluidics channel 662, suction channel 136 and exit at distal opening 168. Vacuum source 166 via suction conduit 160 may be in fluid communication with fourth fluidics channel 664 such that fluid or material at the target site are pulled through distal opening 158 and flow through fluid channel 134, second fluidics channel 654, connecting tube 690, and fourth fluidics channel 664 toward and/or into vacuum source 166. As shown in FIG. 6B, pinch portion 692 may be in an uncompressed state. Lumen 618 may have a diameter or other cross-sectional dimension greater than or equal to that of pinch portion 692. When pinch portion 692 is received within lumen 618, pinch portion 692 may be in the uncompressed state and permit fluid flow through connecting tube 690 into fourth fluidics channel 664.

Valve assembly 600 may be positioned within handle 120 such that an end (e.g., first end 602) of inner body 610 extends through aperture 121*a* of housing 121. End 602 of inner body 610 extending through the aperture of the housing may be an actuator of handle 120. To transition valve assembly 600 from the first configuration to the second configuration, the user may press end 602 to slide inner body 610 relative to outer body 640. Optionally, valve assembly 600 may include a biasing element similar to valve assembly 300 or 400 configured to automatically transition valve assembly 600 from the second configuration to the first configuration when the user is no longer applying force to the portion of inner body 610. For example, valve assembly 600 may include a biasing element (e.g., a spring) biased against a surface of inner body 610 (e.g., a surface at second end 604). The biasing element may be configured to automatically transition valve assembly 600 from the second configuration to the first configuration and thereby automatically transition pinch portion 692 from the uncompressed state to the compressed state so that fluid flow is permitted through tube 690 into fourth fluidics channel 664.

While principles of this disclosure are described herein with reference to illustrative examples, it should be understood that the disclosure is not limited thereto. Those having ordinary skill in the art and access to the teachings provided herein will recognize additional modifications, uses, examples, and substitution of equivalents all fall within the scope of this disclosure.

What is claimed is:

1. A medical device comprising:

a handle comprising a first conduit and a second conduit each coupled to a valve assembly within a housing of the handle, the valve assembly comprising:

an outer body including a first fluidics channel adjacent to a third fluidics channel on a first side of the outer body; and a second fluidics channel adjacent to a fourth fluidics channel on a second side of the outer body opposite the first side; and an inner body movable within the outer body;

wherein the valve assembly includes a first configuration in which the first fluidics channel and the second fluidics channel are in fluid communication with each other and with the first conduit, and the third fluidics channel and the fourth fluidics channel are in fluid communication with each other and with the second conduit;

wherein the valve assembly includes a second configuration in which the first fluidics channel and the third fluidics channel are in fluid communication with each other and with the first conduit, and the second fluidics channel and the fourth fluidics channel are in fluid communication with each other and with the second conduit; and wherein moving the inner body relative to the outer body transitions the valve assembly between the first configuration and the second configuration.

2. The medical device of claim 1, wherein the inner body is slidable within an opening of the outer body.

3. The medical device of claim 1, wherein the inner body is rotatable relative to the outer body within an opening of the outer body.

4. The medical device of claim 1, wherein an end of the inner body defines an actuator of the handle, the end being coupled to the housing of the handle and configured to receive user input to transition the valve assembly between the first configuration and the second configuration.

5. The medical device of claim 1, wherein one of the first conduit or second conduit includes a port configured to be coupled to a source of fluid, and the other of the first conduit or second conduit includes a port configured to be coupled to a vacuum source.

6. The medical device of claim 1, wherein the housing includes a fluid inlet and an aspiration outlet, the fluid inlet being connected to the first fluidics channel and the aspiration outlet being connected to the fourth fluidics channel in both the first configuration and the second configuration of the valve assembly.

7. The medical device of claim 6, further comprising a shaft coupled to the handle, the shaft defining a fluid channel and a suction channel each coupled to the valve assembly.

8. The medical device of claim 1, wherein the inner body defines two first lumens with portions parallel to each other, and in the first configuration, one of the first lumens is in fluid communication with the first conduit and the other of the first lumens is in fluid communication with the second conduit.

9. The medical device of claim 8, wherein the inner body defines two second lumens with portions parallel to each other, and in the second configuration, one of the second lumens is in fluid communication with the first conduit and the other of the second lumens is in fluid communication with the second conduit.

10. The medical device of claim 9, wherein the two first lumens are perpendicular to portions of the second two lumens.

11. The medical device of claim 9, wherein the two first lumens are staggered with the two second lumens.

12. The medical device of claim 1, wherein the inner body defines two first lumens extending along an outer surface of the inner body, and in the first configuration, one of the first lumens is in fluid communication with the first conduit and the other of the first lumens is in fluid communication with the second conduit.

13. The medical device of claim 1, wherein the valve assembly includes a biasing element that biases the inner body to the first configuration.

14. A medical device comprising:

a handle comprising a first conduit and a second conduit each coupled to a valve assembly within a housing of the handle, the valve assembly comprising:

an outer body including a first fluidics channel adjacent to a third fluidics channel on a first side of the outer body; and a second fluidics channel adjacent to a fourth fluidics channel on a second side of the outer body opposite the first side; and an inner body slidable or rotatable within the outer body, an end of the inner body being coupled to the housing and configured to receive user input;

wherein the valve assembly includes a first configuration in which the first fluidics channel and the second fluidics channel are in fluid communication with each other and with the first conduit, and the third fluidics channel and the fourth fluidics channel are in fluid communication with each other and with the second conduit;

wherein the valve assembly includes a second configuration in which the first fluidics channel and the third fluidics channel are in fluid communication with each other and with the first conduit, and the second fluidics channel and the fourth fluidics channel are in fluid communication with each other and with the second conduit; and wherein moving the inner body relative to the outer body by user input transitions the valve assembly between the first configuration and the second configuration.

15. The medical device of claim 14, wherein the housing includes a fluid inlet and an aspiration outlet, the fluid inlet being connected to the first fluidics channel and the aspiration outlet being connected to the fourth fluidics channel in both the first configuration and the second configuration of the valve assembly.

16. The medical device of claim 14, wherein the valve assembly includes a biasing element that biases the inner body to the first configuration.

17. The medical device of claim 14, wherein the inner body defines two first lumens parallel to each other and two second lumens parallel to each other, and wherein in the first configuration, one of the first lumens is in fluid communication with the first conduit and the other of the first lumens is in fluid communication with the second conduit.

18. The medical device of claim 17, wherein the two first lumens are transverse to the second two lumens.

19. A medical device comprising:

a handle comprising a first conduit and a second conduit each coupled to a valve assembly within a housing of the handle, the housing including a fluid inlet and an aspiration outlet, wherein the valve assembly comprises:

an outer body including a first fluidics channel and a third fluidics channel on a first side of the outer body; and a second fluidics channel and a fourth fluidics channel on a second side of the outer body opposite the first side; and an inner body movable within the outer body;

wherein the valve assembly includes a first configuration in which the first fluidics channel and the second fluidics channel are in fluid communication with each other and with the first conduit, and the third fluidics channel and the fourth fluidics channel are in fluid communication with each other and with the second conduit;

wherein the valve assembly includes a second configuration in which the first fluidics channel and the third fluidics channel are in fluid communication with each other and with the first conduit, and the second fluidics channel and the fourth fluidics channel are in fluid communication with each other and with the second conduit;

wherein moving the inner body relative to the outer body by user input transitions the valve assembly between the first configuration and the second configuration; and wherein the fluid inlet being is connected to the first fluidics channel and the aspiration outlet is connected to the fourth fluidics channel in both the first configuration and the second configuration.

20. The medical device of claim 19, wherein the inner body is rotatable relative to the outer body within an opening of the outer body, an end of the inner body being coupled to the housing of the handle and configured to receive user input to transition the valve assembly between the first configuration and the second configuration.

* * * * *